(12) United States Patent
Miller et al.

(10) Patent No.: US 10,687,805 B2
(45) Date of Patent: Jun. 23, 2020

(54) APPARATUS AND METHODS FOR CLAMPING TISSUE LAYERS AND OCCLUDING HOLLOW VESSELS

(71) Applicant: Amsel Medical Corporation, Cambridge, MA (US)

(72) Inventors: Arnold Miller, Cambridge, MA (US); Raanan Miller, Cambridge, MA (US); Nir Lilach, Kfar Yehoshua (IL)

(73) Assignee: Amsel Medical Corporation, Cambridge, MA (US)

( * ) Notice: Subject to any disclaimer, the term of this patent is extended or adjusted under 35 U.S.C. 154(b) by 313 days.

(21) Appl. No.: 15/783,610

(22) Filed: Oct. 13, 2017

(65) Prior Publication Data

US 2018/0042607 A1    Feb. 15, 2018

Related U.S. Application Data

(63) Continuation-in-part of application No. 15/380,245, filed on Dec. 15, 2016, now abandoned, which is a continuation-in-part of application No. 15/226,577, filed on Aug. 2, 2016, now abandoned.

(60) Provisional application No. 62/361,547, filed on Jul. 13, 2016, provisional application No. 62/306,932, filed on Mar. 11, 2016, provisional application No. 62/303,071, filed on Mar. 3, 2016, provisional application No. 62/299,662, filed on Feb. 5, 2016, provisional application No. 62/299,444, filed on Feb.
(Continued)

(51) Int. Cl.
| | | |
|---|---|---|
| A61B 17/122 | (2006.01) | |
| A61B 17/064 | (2006.01) | |
| A61B 17/072 | (2006.01) | |
| A61B 17/10 | (2006.01) | |
| A61B 17/068 | (2006.01) | |
| A61B 17/00 | (2006.01) | |

(52) U.S. Cl.
CPC ...... *A61B 17/0643* (2013.01); *A61B 17/0644* (2013.01); *A61B 17/0686* (2013.01); *A61B 17/072* (2013.01); *A61B 17/105* (2013.01); *A61B 17/1222* (2013.01); *A61B 17/122* (2013.01); *A61B 2017/00243* (2013.01); *A61B 2017/0641* (2013.01); *A61B 2017/0647* (2013.01); *A61B 2017/0688* (2013.01)

(58) Field of Classification Search
CPC ... A61B 17/12; A61B 17/122; A61B 17/1222; A61B 17/128; A61B 17/1285; A61B 17/064; A61B 17/0643; A61B 17/0644; A61B 17/068; A61B 17/0686; A61B 17/072; A61B 17/105; A61B 17/115; A61B 2017/0688; A61B 2017/0641; A61B 2017/0647; A61B 2017/00243
See application file for complete search history.

(56) References Cited

U.S. PATENT DOCUMENTS

| | | | |
|---|---|---|---|
| 5,865,791 A | 2/1999 | Whyte | |
| 2004/0044364 A1* | 3/2004 | DeVries | A61B 17/064 |
| | | | 606/213 |

(Continued)

*Primary Examiner* — Melanie R Tyson
(74) *Attorney, Agent, or Firm* — Bookstein IP Law; Arthur Z. Bookstein (57) ABSTRACT

Apparatus and methods for clamping tissue layers and occluding hollow anatomical structures utilize a pair of implants, each having deployable radially extending legs that clamp the layers together. The implants are locked together by a separate pin that also transfixes the tissue layers.

31 Claims, 11 Drawing Sheets

Related U.S. Application Data

24, 2016, provisional application No. 62/276,042, filed on Jan. 7, 2016, provisional application No. 62/203,655, filed on Aug. 11, 2015, provisional application No. 62/267,825, filed on Dec. 15, 2015, provisional application No. 62/267,883, filed on Dec. 15, 2015, provisional application No. 62/298,724, filed on Feb. 23, 2016.

(56) References Cited

U.S. PATENT DOCUMENTS

| | | |
|---|---|---|
| 2005/0267529 A1 | 12/2005 | Crockett |
| 2012/0283758 A1* | 11/2012 | Miller .............. A61B 17/00008 606/158 |

* cited by examiner

APPARATUS AND METHODS FOR CLAMPING TISSUE LAYERS AND OCCLUDING HOLLOW VESSELS

CROSS-REFERENCE TO RELATED APPLICATIONS

This application is a continuation-in-part and claims the benefit of and priority to U.S. application Ser. No. 15/380,245, filed Dec. 15, 2016 and U.S. application Ser. No. 15/226,577, and other prior applications as set forth in an Application Data Sheet filed concurrently with this application, the entire contents of each of which are incorporated by reference herein in their entireties.

FIELD OF THE INVENTION

The invention generally relates to apparatus and methods for clamping tissue layers and for occluding hollow body structures and is described, for example, in a context of occluding or resecting an atrial appendage.

BACKGROUND

Embolic stroke is among the leading mortality factors for adults, and is a major cause of disability. A common cause of embolic stroke is the release of thrombus that may form in the left atrial appendage ("LAA") as a result of atrial fibrillation. The LAA is a small windsock-like cavity that extends from the lateral wall of the left atrium of the heart, generally at the level between the mitral valve and the root of the left pulmonary vein. The LAA normally contracts with the left atrium during systole so that blood in the LAA is ejected into the left atrium and then into the left ventricle. During atrial fibrillation, however, the LAA fails to vigorously contract due to the lack of synchronicity of the electrical signals in the left atrium. As a result, blood may stagnate within the LAA and thrombus may form in the stagnant blood that pools within the LAA. That thrombus eventually may subsequently be ejected into systemic circulation after a normal sinus rhythm is reinstituted, potentially traveling to the brain and resulting in a stroke.

When treated surgically, the entry to the LAA is obstructed to prevent blood flow between the atrium and the LAA. This may be accomplished in a number of ways, for example, by filling the atrial appendage with a biocompatible material, or by securing a plug in the ostium of the LAA, or by suturing or stapling the opposing walls of the appendage together, after which the LAA may be resected and removed.

Challenges exist for isolating or removing the LAA. For example, the LAA tissue may vary in thickness, with some parts being extremely thin or friable and susceptible to tearing. Consequently, traditional methods of suturing or stapling may present a high risk of bleeding at the puncture site. Moreover, LAA procedures typically are performed as an adjunct to more comprehensive surgical procedures, when the patient is on a heart-bypass machine, and bleeding associated with the typical open or thorascopic methods of occlusion of the LAA generally does not become apparent until the patient is taken off the machine and the heart begins pumping again. If bleeding does occur through the suture or staple puncture points, the patient may need to be put back on the bypass machine to stop the bleeding which exposes the patient to significant additional risk and morbidity.

Known methods for preventing such problems with the LAA have drawbacks. In particular, most of the previously-known devices are designed for a theoretically ideal LAA anatomical structure having a well-defined, symmetrical, and typically circular ostium and expected depth and orientation of the LAA cavity. Such ideal anatomical geometry is rarely, if ever, encountered. Among the devices currently in use is a hairpin-shaped clip (Ligaclip) that may be placed exteriorly over the juncture of the LAA and atrium so that the legs of the clip can be deformably squeezed together along the juncture. Such clips have been reported, in some instances, to fail to fully occlude the hollow structure to which they were applied. Other devices that employ a loop applied to the base of the LAA on the pericardial surface may abrade the pericardial surface, potentially leading to fatal cardiac pericarditis or pericardial tamponade. Other devices involve using expandable disks to clamp and collapse the LAA tissue, but these, too, rely on the LAA having reasonably symmetric and well-defined depth and anatomy and have issues around sealing at tissue puncture points. There remains a need for devices and techniques for occluding hollow anatomical structures such as, for example, the LAA, that avoid the foregoing difficulties.

SUMMARY

In accordance with the invention, devices and methods are provided for clamping tissue to isolate an atrial appendage or other hollow anatomical structures. The devices and methods can be employed during open surgery or thoracoscopy. The clamping devices transfix the opposing walls of the hollow anatomical structure, such as the LAA, and, for example, can be placed in a row (either aligned or out of alignment) along the base of the LAA where it joins to the atrial wall, to occlude flow between the LAA and the left atrium. Unlike prior art clips, the clamps can be precisely deployed at the desired locations, including in a non-linear pattern that follows the contours of the junction between the LAA and atrial wall to occlude the LAA ostium. The clamps include radially extending legs that can flex when engaging tissue so that they can self-accommodate to varying tissue thicknesses of the walls of the LAA. Additionally, the legs of the clamps utilize an interdigitating configuration that is effective to clamp tissue circumferentially about the transfixion point and constrain the tissue in a serpentine configuration to make an effective, non-leaking seal about the point of transfixion. The occluded LAA can be left in place, or it can be subsequently resected. The occlusion devices can also be used to close surgical incisions in fragile tissue such as the atria, which commonly experience post-operative bleeding with the use of regular sutures. In another aspect of the invention a protective cap may be provided on portions of the clamp to prevent injury to adjacent tissue.

In practicing the invention to occlude an LAA, the LAA may be elevated or isolated from the rest of the heart, for example, by using a sling made from synthetic material or animal tissue. The sling can be a noose-like or lasso-like structure of adjustable width that wraps around the base of the LAA and can be tightened with an adjustable tightening member to fit snugly around the LAA.

While the following description is provided in the context of isolating a left atrial appendage, it should be understood that the invention is useful for other, similar procedures such as occluding the right atrial appendage (RAA), as well as other cardiac and vascular procedures, including atrial incision, atrial volume reduction, ventricular aneurysms, arterial plication for the aortic ectasia or pulmonary artery, cholecystectomy, and numerous other laparoscopic or open procedures to close off vessels, clamp tissues, or any procedures that involve occluding, suturing, resecting, amputating, or stopping blood or fluid flow. Clamping devices and methods for sealing the region surrounding a tissue puncture site or transfixion point are described in U.S. patent publication 2015/0173765, the disclosure of which is incorporated herein by reference.

The invention provides methods for occluding a hollow body structure such as an atrial appendage by deploying a plurality of clamping devices transfixing a first wall and a second wall of an atrial appendage. In some embodiments, the method involves simultaneously deploying an array of a plurality of clamps. In other embodiments, the method includes deploying individual clamping elements each of which transfixes a distal wall and a proximal wall, and locking the clamping elements together thereby occluding the hollow structure.

In the following description, it should be understood that terms such as "upper," "lower," "front," "back," "forward and "rearward"are used in a relative sense and for convenience to indicate the relative position or direction of a particular component or function.

DETAILED DESCRIPTION

The present invention provides devices and methods for clamping tissue layers together to occlude hollow anatomical structures. Although described in the context of isolating a left atrial appendage the invention may be used to perform other procedures where a hollow anatomical structure is to be occluded or isolated. The terms "tubular structure," "hollow structure" and "vessel" may be used interchangeably to mean hollow anatomical structures that can be occluded, including the LAA. The invention can be employed during open surgery or thoracoscopy. In the context of the LAA, the invention generally involves placing occlusion clamps along the base of the LAA, that is, at the juncture of the LAA with the wall of the left atrium, to prevent blood flow between the LAA and the atrium. Once isolated, the LAA may be subsequently resected.

Figure 1:
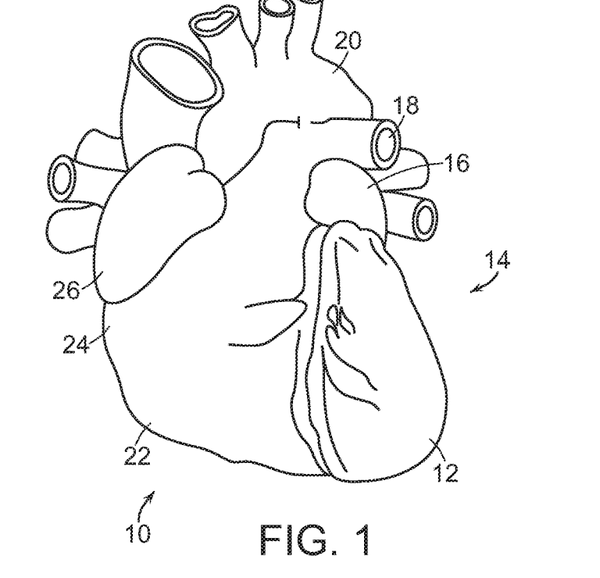
FIG. 1 is a diagrammatic illustration of a human heart.

FIG. 1, illustrates, diagrammatically, the exterior of a heart including the left ventricle 12, left atrium 14, left atrial appendage (LAA) 16, pulmonary artery 18, the aorta 20, the right ventricle 22, the right atrium 24, and the right atrial appendage 26. The left atrium 14 is located above the left ventricle 12 and the two are separated by the mitral valve within the heart. The LAA 16 is normally in fluid and electrical communication with the left atrium 14 such that blood flows in and out of the LAA, in synchrony with the atrium as the heart 10 beats.

Figure 2A:
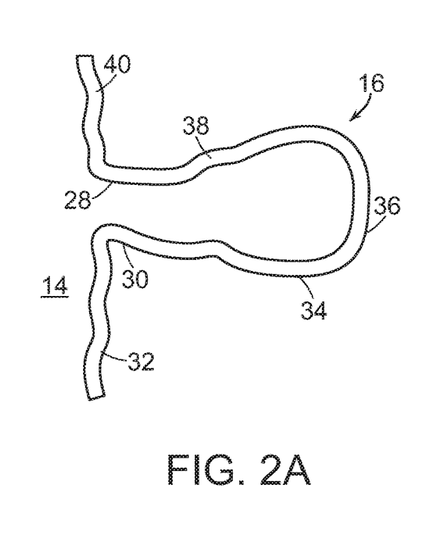
FIGS. 2A and 2B are diagrammatic cross sectional views of a left atrial appendage.
Figure 2B:
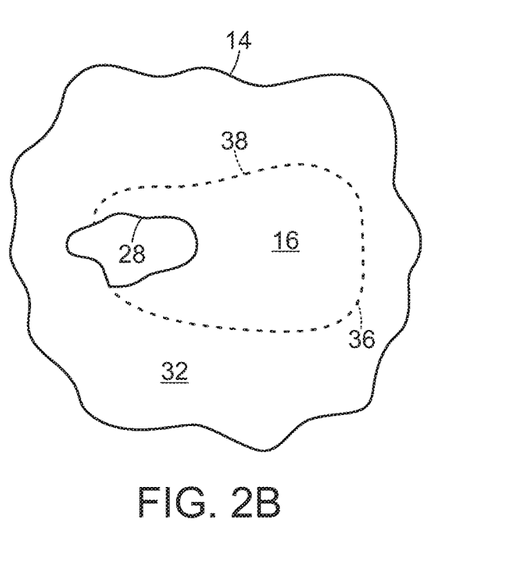

FIGS. 2A and 2B are, respectively, a diagrammatic cross section of an LAA 16 and a plan view of the ostium 28 to the LAA. The chamber of the left atrium 14 and the interior of LAA 16 are shown in communication via ostium 28. The LAA is further defined as having base portion 30 where it attaches to pericardial surface 32 of the left atrium 14, and body portion 34 extending from the base of LAA 16 with the left atrium, including apex 36. The walls 38 of LAA 16 are vascularized heart tissue generally similar to the walls 40 of the left atrium. As shown in FIG. 2B, ostium 28 may have an irregular circumference, and body portion 34 of the LAA may extend from the left atrium at a shallow angle lying close to the atrium, making it difficult to implant a circular occlusive member or hairpin-type clip about the base of the LAA. Generally, the length of occlusion required may be of the order of about approximately 3-4 cm. The walls 38 of the LAA may have portions that vary in thickness as well as in resistance to tearing. Fragile tissue may be damaged by traditional methods of suturing or stapling, leading to excessive bleeding. Thus, it is desirable to occlude the LAA in a manner that can adapt to varying wall thickness while minimizing the forces needed to effect occlusion. In some cases, the LAA 16 may be amputated after occlusion has been completed. The LAA 16 can be amputated at or near the position of the occluders. The procedure can be performed on a beating or non-beating heart. The present invention provides a device that can occlude the LAA while reducing the risk of damage.

Although the LAA is illustrated in FIG. 2A, for convenience of explanation, as extending approximately perpendicular to the left atrium, more commonly the LAA may lie closely adjacent the outer surface of the atrium. Optionally, a sling or other surgical implement can be used to elevate the LAA away from the heart to provide better access to the underside of the LAA. In some procedures, the method may include encircling the atrial appendage with a sling to lift the atrial appendage away from other heart tissue. In other techniques, a sling may be used to support and reinforce the hollow anatomical structure when the occluder element is deployed through the sling and the tissue. The sling can be made of a synthetic polymer or animal tissue and it can include a suture and an adjustable member in a noose configuration. The atrial appendage may be occluded with the sling before deploying the occluder. In some procedures, a protective device can be placed between the atrial appendage and the other heart tissue or veins and arteries to protect them. The devices may have a polymeric or organic coating to prevent rubbing against surrounding tissue and causing erosion or damage.

Figure 3:
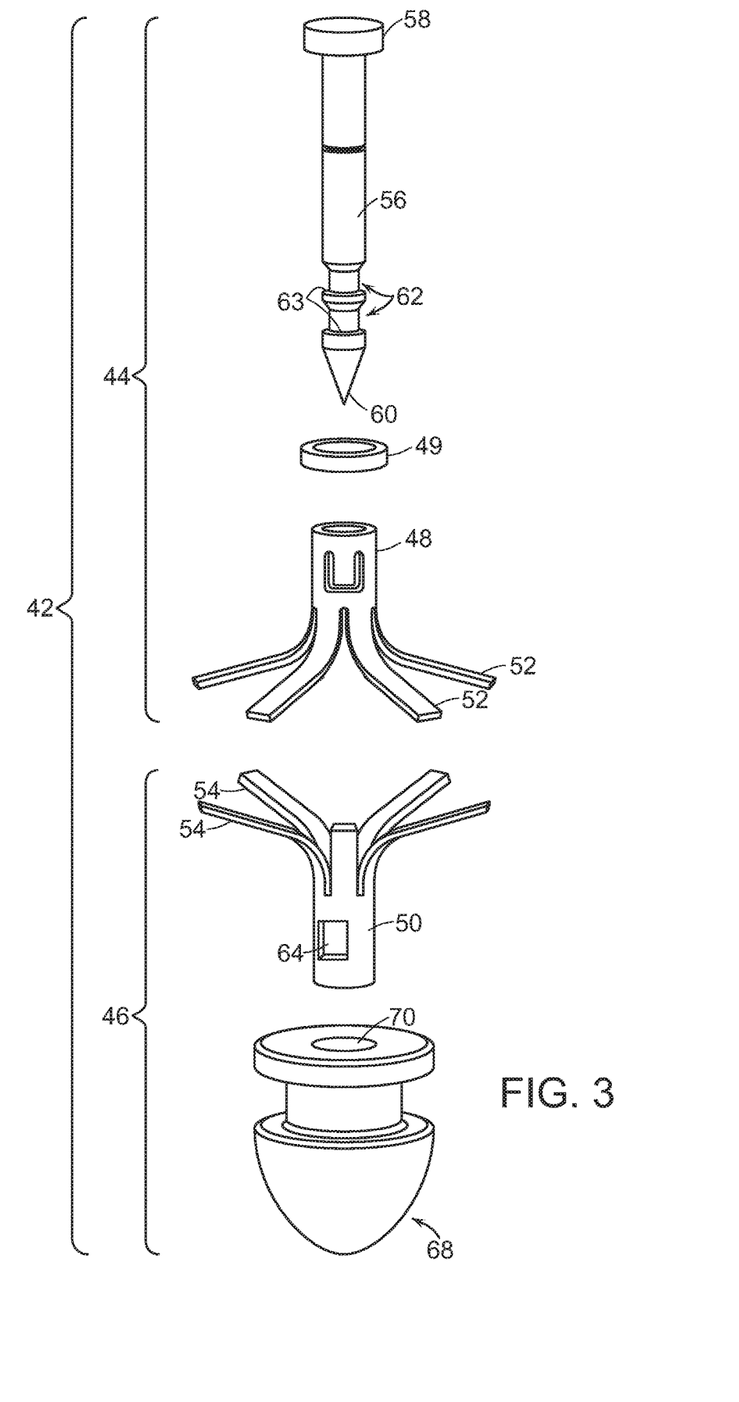
FIG. 3 is an exploded illustration of an embodiment of a tissue clamp as may be used in practicing the invention.
Figure 7:
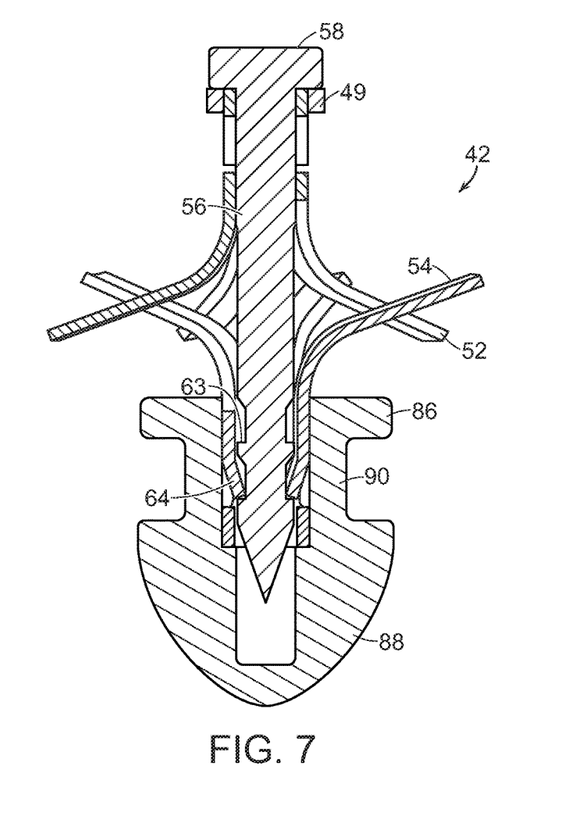
FIG. 7 is a sectional illustration of a tissue clamp in its deployed configuration and showing how the upper and lower implants are locked together and with the legs of the implants interdigitated.
Figures 12, 12A:
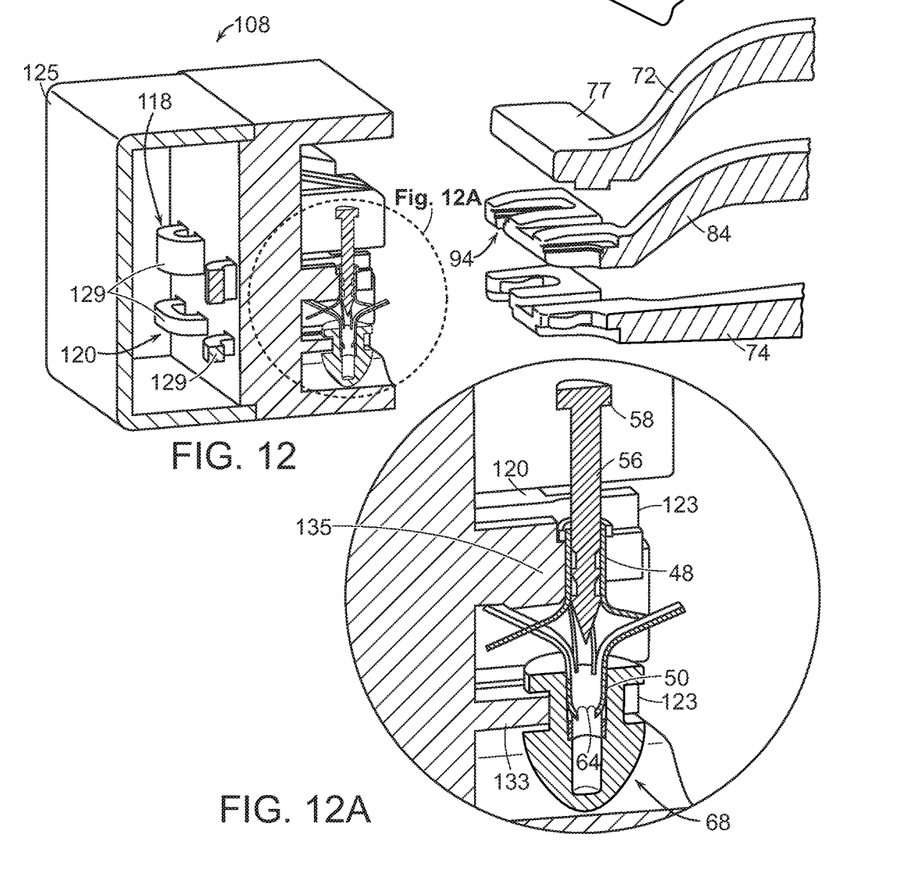
FIG. 12 is an isometric sectional illustration of the forward end of the jaws of the deployment tool and the cartridge as the jaws approach the cartridge and sectioned along the plane 12-12 of FIG. 11.
FIG. 12A is an enlarged portion of FIG. 12 showing the manner in which the lower implant is retained in the cartridge in readiness to be transferred to the deployment tool.
Figure 13:
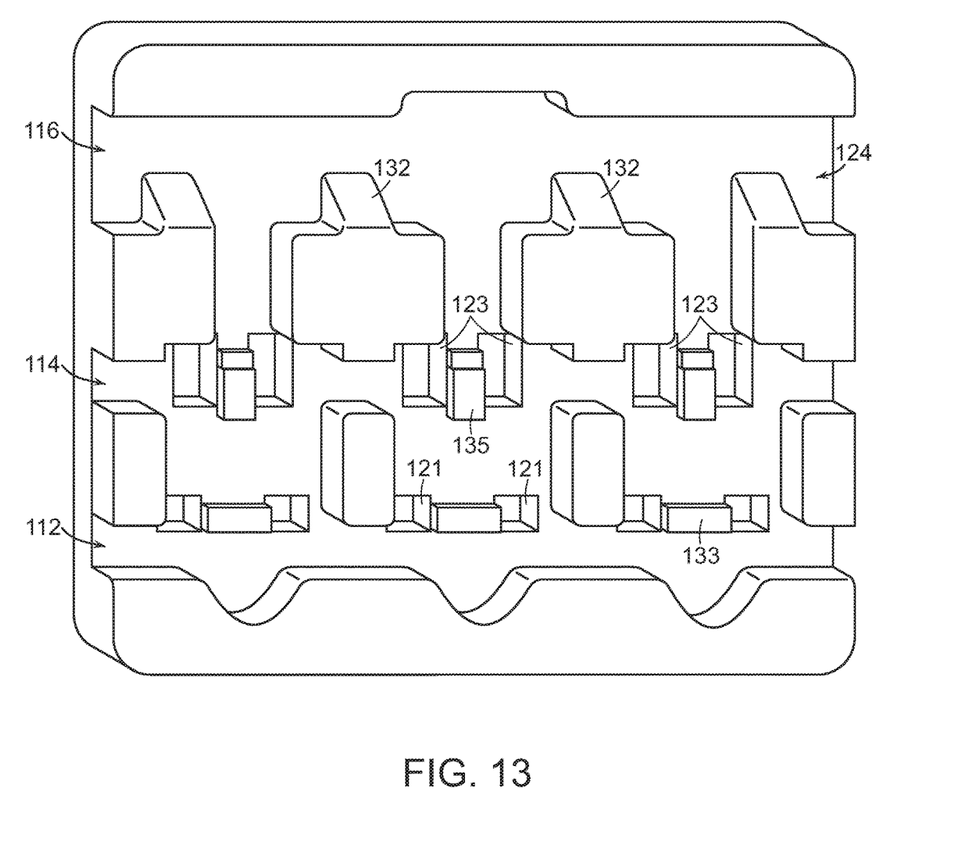
FIG. 13 is an isometric illustration of the front portion of the cartridge with the implants removed.
Figure 13A:
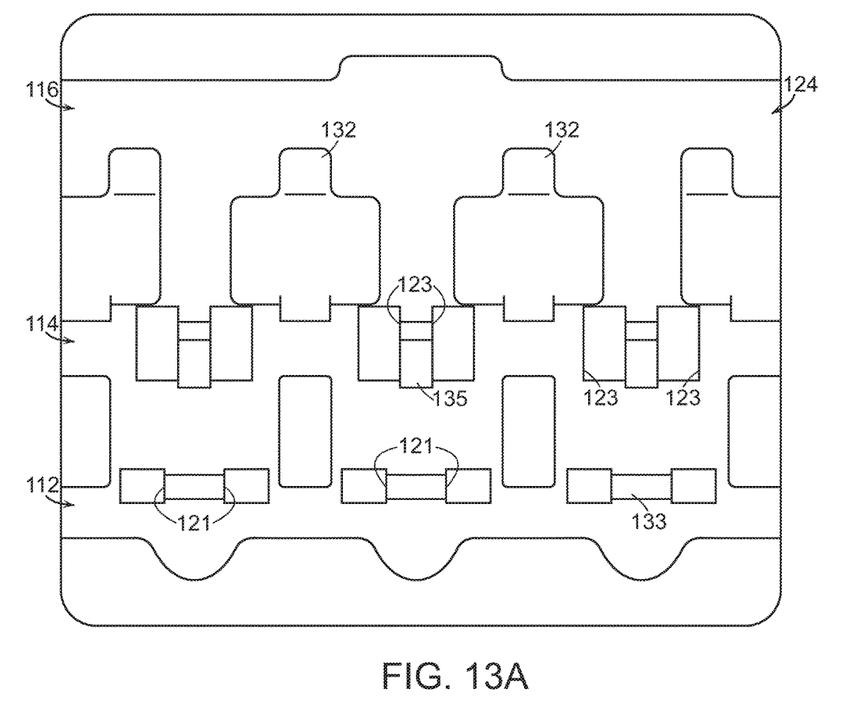
FIG. 13A is an elevation illustration of the front facing portion of the cartridge with the implants removed.
Figure 14:
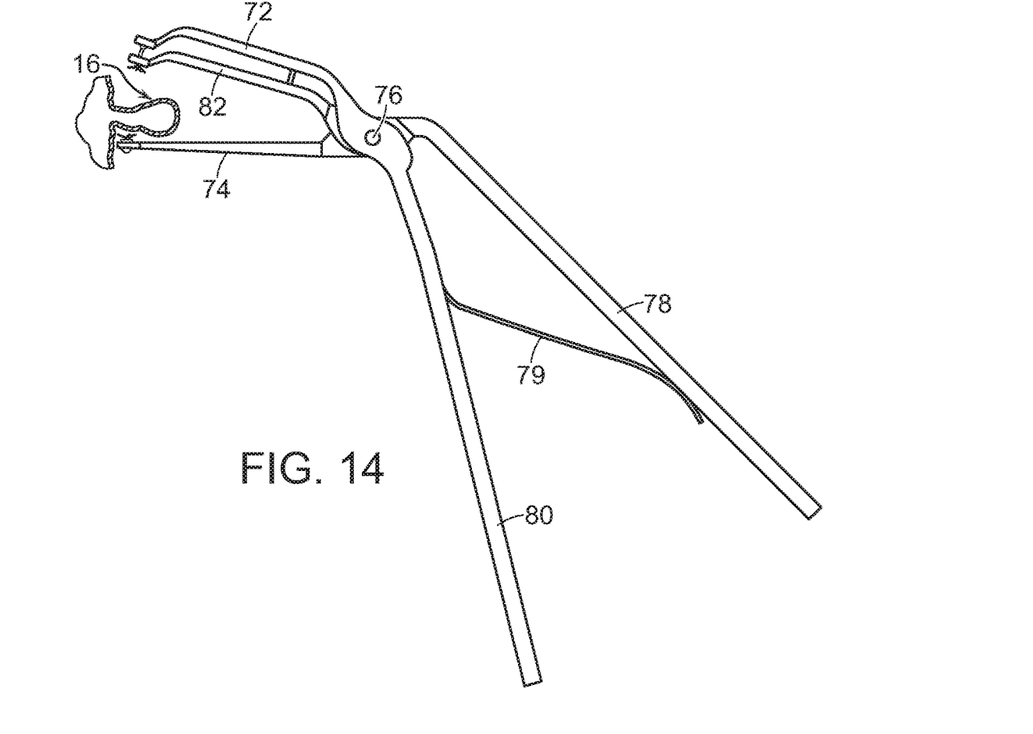
FIG. 14 is a side view of a deployment tool in a configuration receptive to a hollow anatomical structure such as a LAA.
Figure 17:
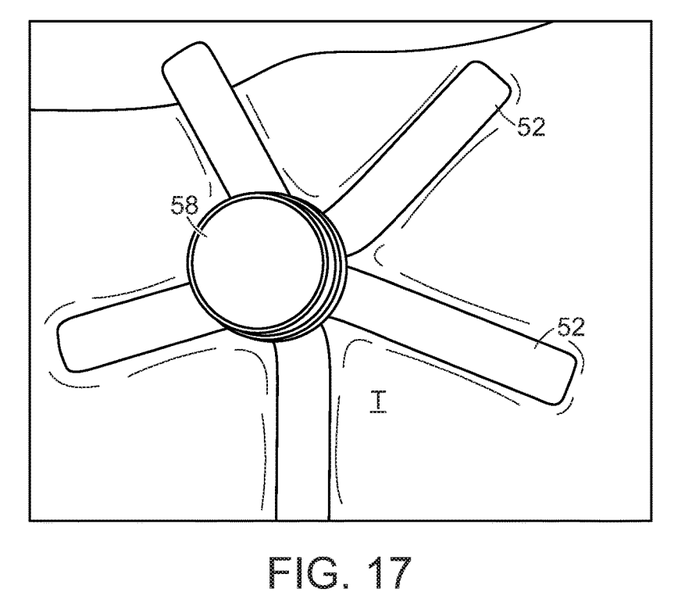
FIGS. 17 and 18 illustrate, respectively in plan and in elevation, the tissue clamp attached to a tubular vessel showing the manner in which the interdigitated legs of the implants constrain the clamped tissue in a serpentine configuration.
Figure 18:
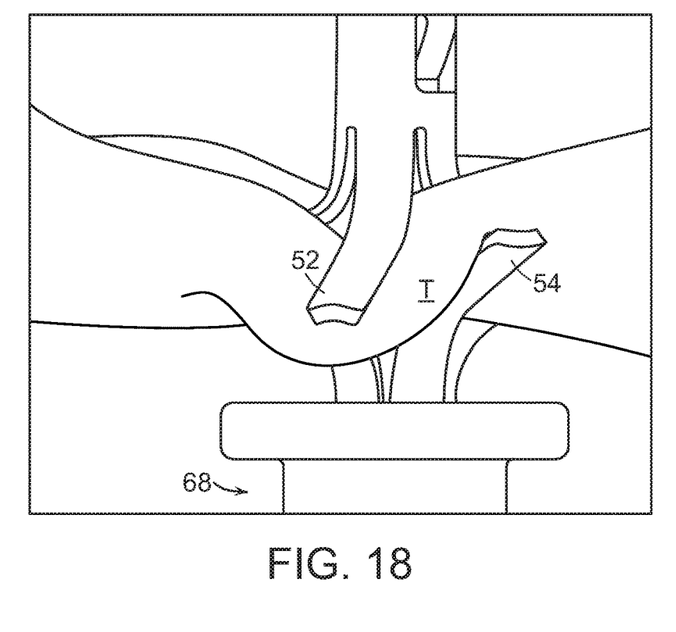

FIG. 3 is an exploded illustration of the components of a tissue clamp 42 as may be used in practicing the invention. The tissue clamp 42 includes an upper implant 44 and a lower implant 46 that cooperate to engage and press together the opposing walls of the LAA or another hollow anatomical vessel to cause it to be occluded. Each of the implants has a tubular body 48, 50, respectively, and a plurality of radially extending legs 52, 54, respectively. The implants may be formed from a resilient material such as a superelastic nickel-titanium alloy (e.g., Nitinol) so that the legs can flex to accommodate tissue of varying thickness while having sufficient stiffness to shape the engaged tissue as described below. The legs 52, 54 of the implants are arranged so that they are out of registry with the legs of the opposing implant when the implants are brought together with the legs of the implants being interdigitated as shown in FIGS. 7, 12 and 12A. The legs of at least one and preferably both implants define a generally conical or concave configuration so that when the concavities face each other, the legs can interdigitate in the absence of tissue (see FIG. 7) and also when tissue is captured between the implants, depending on the thickness of the tissue. Tissue thickness of the LAA walls typically is such that the tissue can conform to the shape defined by the implants. When the clamp 42 engages tissue between the interdigitated legs of the implants, the tissue is constrained in a serpentine configuration as illustrated in FIGS. 17 and 18. We have found that by constraining the tissue in a serpentine pattern, in which the tissue layers are subjected to successive reversals in direction, the opposing tissue layers can be secured together with less potentially damaging force on the tissue than with a direct compressive clamp. Moreover, the serpentine pattern circumscribes the center of the device in a manner that forms a seal that circumscribes the aperture formed in the tissue by a locking pin 56, described below. Additionally, the serpentine pattern and the sealing diameter extends beyond the diameter of the legs 52, 54 such that two or more clamps can be used adjacent, but spaced from each other, to define a sealed length of tissue layers.

As shown in FIG. 3, the tissue clamp also includes a locking pin 56 that extends through the tubular bodies 48, 50 of the implants as well as the tissue layers (e.g., LAA walls 38, 40) to securely clamp the tissue layers together. The locking pin 56 has a head 58 formed at its upper end and a sharp, tissue-piercing tip 60 at its lower end. The locking pin also has a locking element, such as one or more circumscribing grooves 62, formed between its ends. The grooves 62 define shoulders 63 that are adapted to engage other locking elements, such as detents in the form of tabs 64 formed in the body 50 of the lower implant. Engagement of a shoulder 63 with a tab 64 locks the pin 56 to the lower implant and the head 58, which defines a diameter greater than the inner diameter of the upper end of the upper implant, prevents separation of the upper implant from the assembly. Thus, the pin 56 serves to puncture and transfix the tissue layers and locks the clamp components together.

The lower implant 46 may be provided with a tissue guard 68 as may be desirable to protect tissue adjacent the tissue layers being attached or occluded. For example, when occluding the LAA, it may be desirable to protect the outer wall of the left atrium from risk of abrasion or trauma from the lower implant or sharp tip 60 of the pin 56. To that end, the tissue guard 68 preferably is formed to have a smooth external surface and may be bullet-shaped as shown or another suitable shape. The tissue guard 68 is securely attached to the tubular body 50 of the lower implant. The tissue guard has an internal lumen 70 that can receive the sharp tip 60 of the locking pin 56.

Figures 4, 4A:
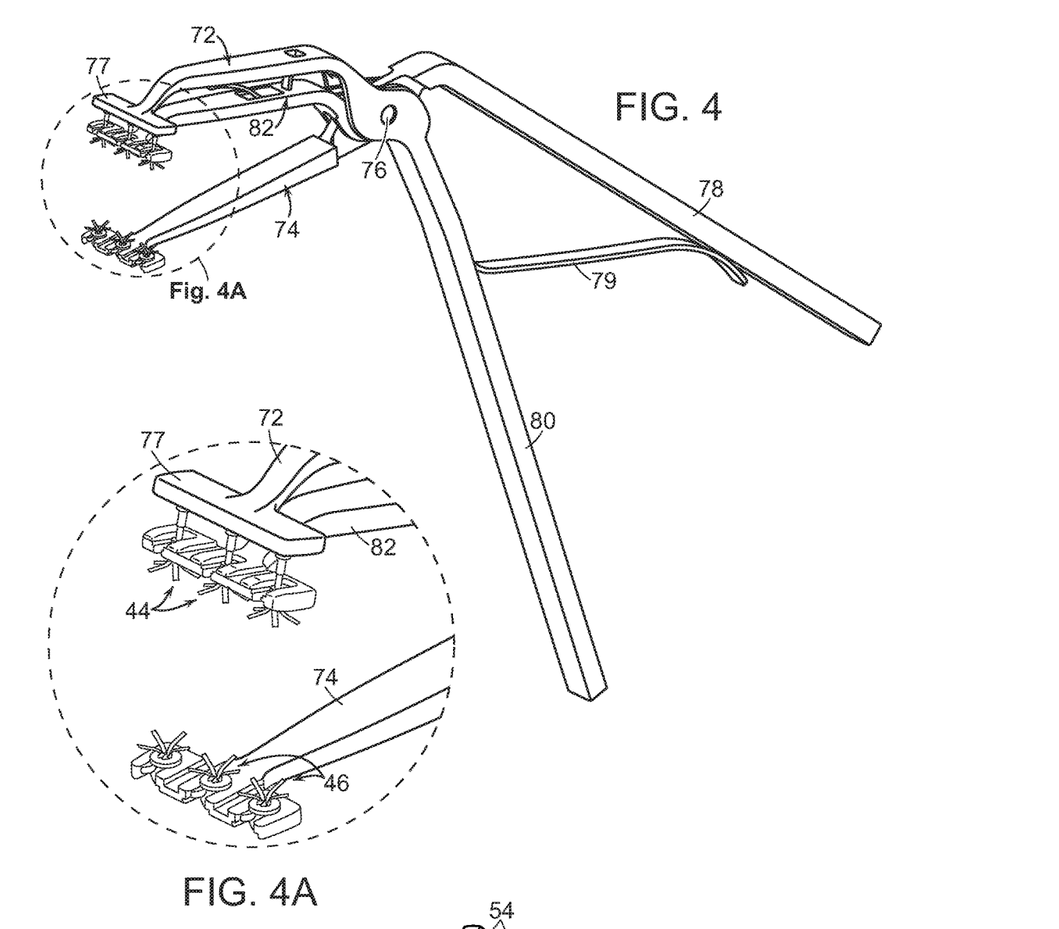
FIG. 4 is an isometric illustration of a deployment tool that may be used to deploy single or multiple clamps to tissue.
FIG. 4A is an enlarged view of the jaws of the deployment tool loaded with upper and lower implants.
Figure 5:
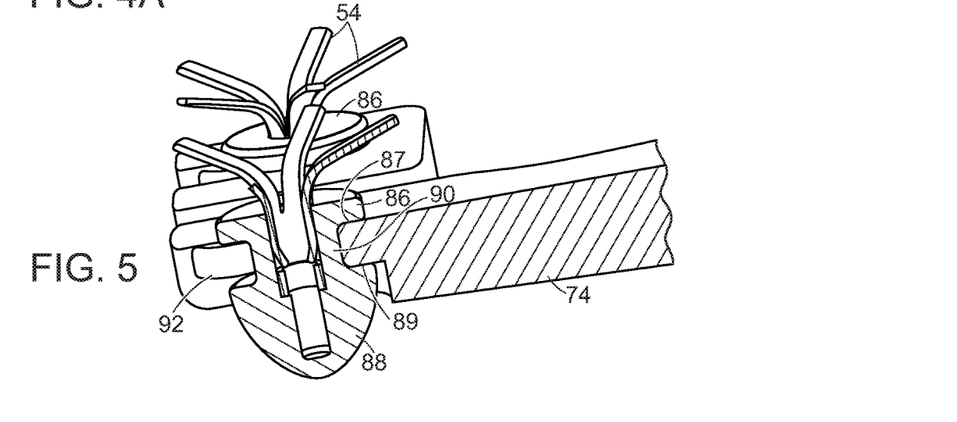
FIG. 5 is an enlarged, sectional illustration of a portion of the lower jaw of the deployment tool loaded with implants.
Figure 6:
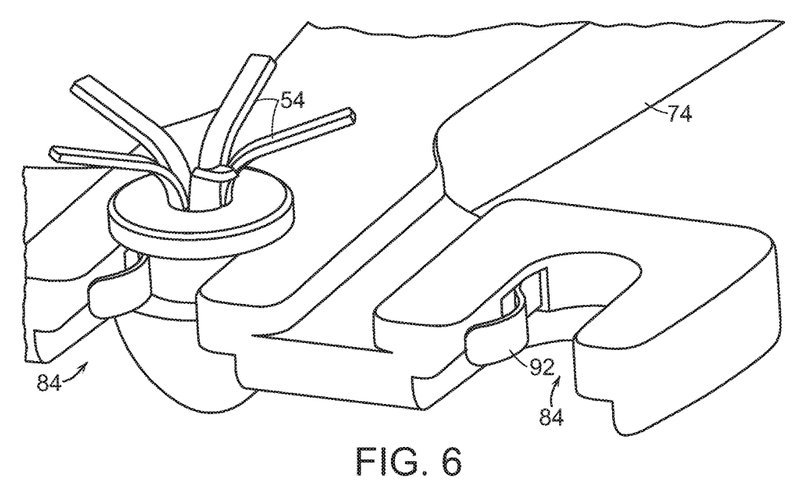
FIG. 6 is an enlarged, isometric illustration of a portion of the lower jaw and a lower implant held in the jaw of a deployment device.

FIGS. 4-6 illustrate a device for deploying several tissue clamps 42 simultaneously, for example, to occlude and isolate an LAA having a wide ostium 28. Although the illustrative embodiment has a capacity of, and is loaded with three such tissue clamps 42, it should be understood that clamps may be deployed individually or in an array containing any number of clamps. The deployment device is somewhat similar in structure as a pliers having an upper jaw 72 and a lower jaw 74 both of which extend forwardly of a pivot 76 and are formed integrally with handles 78, 80. The lower jaw 74 is arranged to hold the subassembly of the lower implant 48 and tissue guard 68. The subassembly of the upper implant 44 and locking pin 56 is supported at the forward end of an intermediate jaw 82 that is pivoted at pivot 76 and does not have a separate handle. The forward end of the upper jaw 72 is adapted to engage the head 58 of the locking pin 56 to drive the pin and upper implant 44 downwardly, to pierce the tissue layers and lock the clamp components together. Each of the jaws may have a transversely extending member at its forward end in order to accommodate a plurality of tissue clamps as illustrated in the drawings. The handles 78, 80 may be biased apart by a leaf spring 79. A leaf spring 81 also may be provided between the upper and intermediate jaws to bias them apart.

FIGS. 5 and 6 show the manner in which the lower jaw 74 holds the lower implant 46. For each lower implant 46, the lower jaw 74 has a forwardly opening slot 84 that receives, removably, and retains a lower implant 46, as by engaging the tissue guard 68 of the lower implant. To that end, the tissue guard may be formed to define an upper portion 86 and a lower portion 88 separated by a waist portion 90. The waist 90 may be dimensioned to be received within the slot 84 of the lower jaw with the upper and lower portions 86, 88 embracing the upper and lower edges 87, 89 of the slot 84 (FIG. 5). A retention spring 92 may be embedded in the lower jaw in association with each slot 84 to engage the waist 90 of the tissue guard sufficiently to hold it, releasably, within the slot until deployed. After the clamp 42 has been deployed, the open-ended slot enables the deployment tool to be withdrawn, leaving the deployed clamp in place, secured to the tissue.

Figure 8:
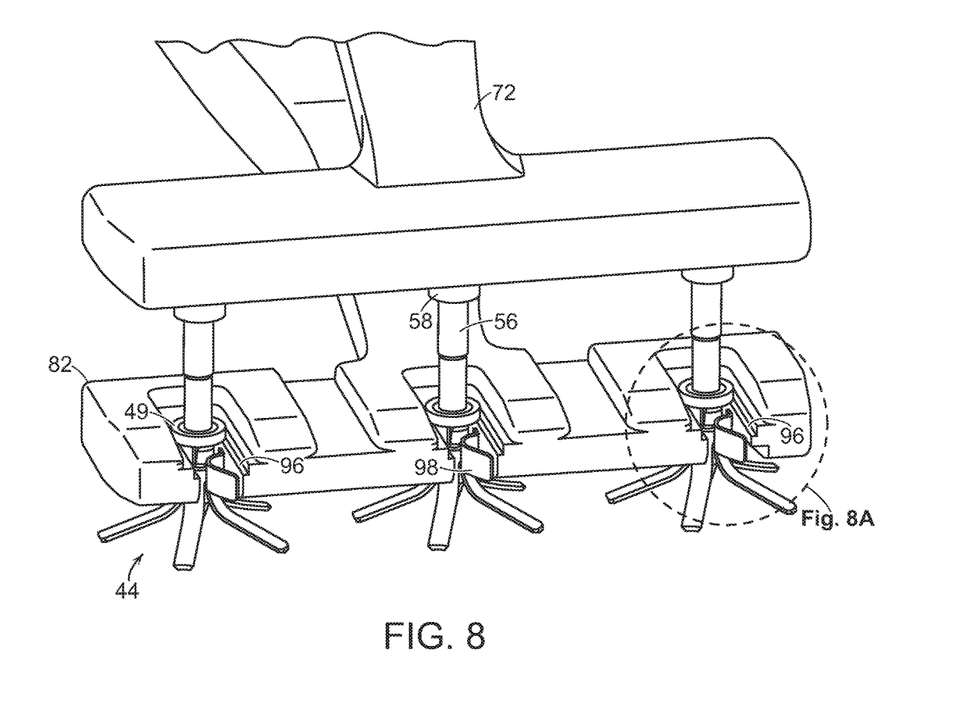
FIG. 8 is an enlarged illustration of the upper and intermediate jaws of the deployment tool, loaded with upper implants.
Figure 8A:
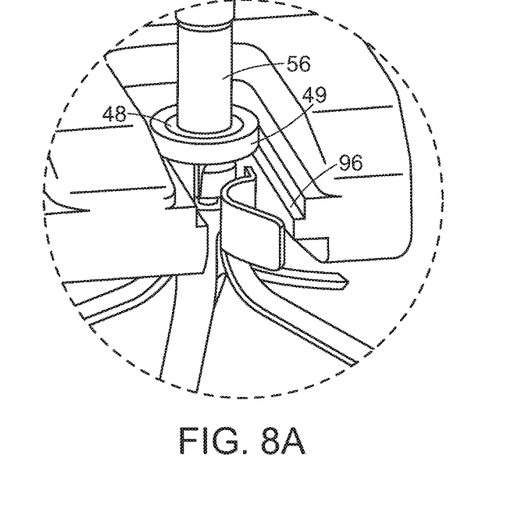
FIG. 8A is an enlarged detail of a portion of FIG. 8.

FIGS. 8 and 8A illustrate the manner in which the upper implant 44 and pin 56 (together, the "upper clamp subassembly") are held in the intermediate jaw 82. The intermediate jaw is formed to have one or more forwardly opening slots 94 similar to the slots 86 in the lower jaw. Each slot 94 is formed with a ledge 96 extending along the upper edge of the slot, the ledge being adapted to provide support for a collar 49 that is integrally attached to the upper end of the tubular body 48 of the upper implant 44. Each slot 94 also is provided with a retention spring 98 embedded in the intermediate jaw 82 and adapted to releasably engage the side of the tubular body 48 of the upper implant 44 contained in the slot 94. The locking pin 56 is retained within the lumen of the tubular body 48 in readiness to be driven downwardly by the pressure pad 77 through the upper implant 44, the tissue layers and the lower implant 46 when the deployment device is operated. After the clamp 42 has been deployed, each open-ended slot 94 enables the deployment tool to be withdrawn, leaving the deployed clamp 42 in place in the tissue.

Figure 9:
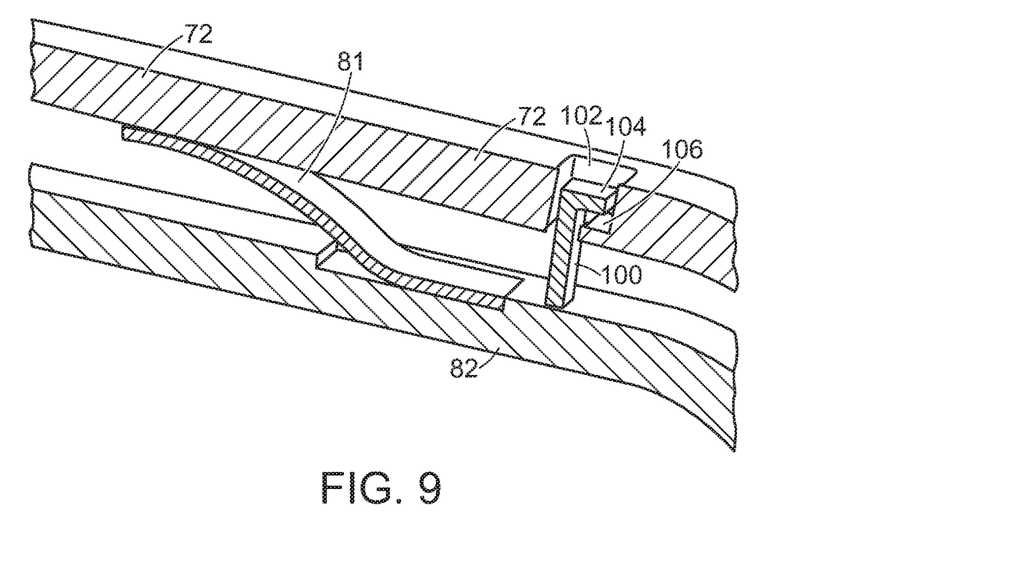
FIG. 9 is an enlarged, sectional illustration of a portion of the upper and intermediate jaws of the deployment tool.

The locking pin 56 is prevented from separating from the upper implant by the transverse pressure pad 77 of the upper jaw 72 that overlies the upper implant subassembly. This may be achieved by limiting the extent of separation of the upper and intermediate jaws 72, 82 so that the space between the head 58 of the pin 56 and the upper jaw is never so much as to allow the pin to pull out of the tubular body 48 of the upper implant 44. The extent of separation may be limited, for example, as shown in FIG. 9 by a post 100 that is secured to the intermediate jaw and extends upwardly through an aperture 102 in the upper jaw. The post 100 may have a catch 104 that engages an upwardly facing surface 106 of the upper jaw to limit the extent to which the upper and intermediate jaws 72, 82 can be separated.

The tissue clamps 42 of the invention may be relatively small devices, for example, of the order of about four or five millimeters in diameter. In order to facilitate loading the tissue clamps into a deployment device, the clamp components preferably are releasably held in a cartridge preloaded with the clamps that can be engaged by the deployment device to transfer the clamp components from the cartridge to the deployment device. As shown in FIGS. 10-14 a cartridge 108 is provided with three sets of tissues clamps 42 and may be used, for example, with a three-clamp deployment tool, as described above, to load one, two or three clamps in the deployment tool. It should be understood, however, that cartridges and deployment tools may be employed to have any number of clamps. The upper and lower implants 44, 46 may be held in the cartridge 108 with their legs 52, 54 being interdigitated as they would be when deployed but in an unlocked configuration, the pin 56 not yet having been driven into locking engagement with the lower implant 46.

Figure 10:
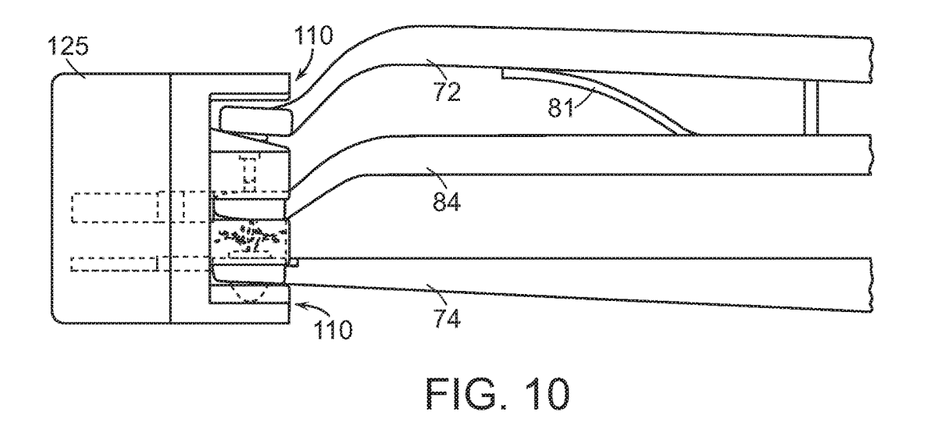
FIG. 10 is a side view of the deployment tool in full engagement with a cartridge as the tissue clamps are transferred from a storage cartridge to the deployment tool.
Figure 11:
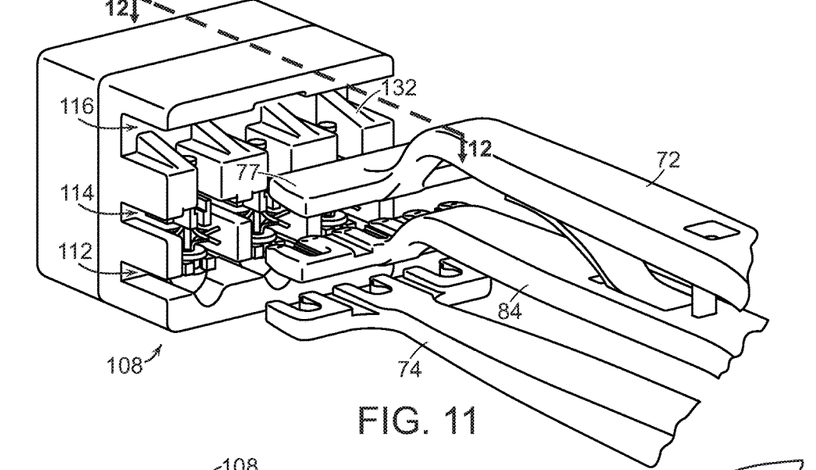
FIG. 11 is an isometric illustration of the jaws of the deployment tool as they approach the front face of the cartridge.

The cartridge may be considered as having a front face 110 that may be aligned with and face the forward ends of the jaws 72, 74, 82, with the front face 110 being formed to define three vertically spaced, transversely extending slots 112, 114, 116 receptive, respectively, to the lower, intermediate and upper jaws 74, 84 and 72. The lower slot 112 is adapted to receive the forward end of the lower jaw 74, the intermediate slot 114 is adapted to receive the forward end of the intermediate jaw 82 and the upper slot 116 is adapted to receive the forward end of the upper jaw 72. The upper and lower implants 44, 46 are held in the cartridge so that when the forward ends of the jaws are inserted into the slots 112, 114, 116 of the cartridge, the slots 84, 94 at the forward ends of the lower jaw 74 and the intermediate jaw 82 will engage and embrace the lower implant 46 and upper implant 44, respectively. After the jaws have engaged the implants they can draw the implants out of the cartridge and be in readiness to be deployed by the deployment device. The springs 92, 98 on the lower jaw 74 and intermediate jaw 84 are formed to grip their respective implants to overcome any resistance to removal of the implants from the cartridge.

Figure 15:
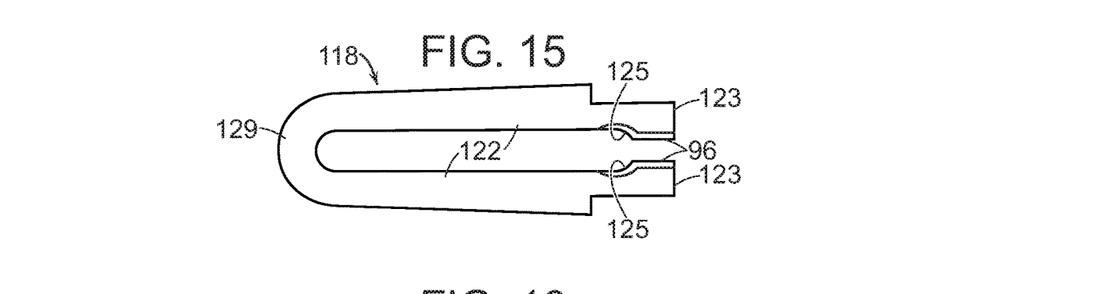
FIG. 15 is a plan view of an upper implant retainer that holds an upper implant in the cartridge.
Figure 16:
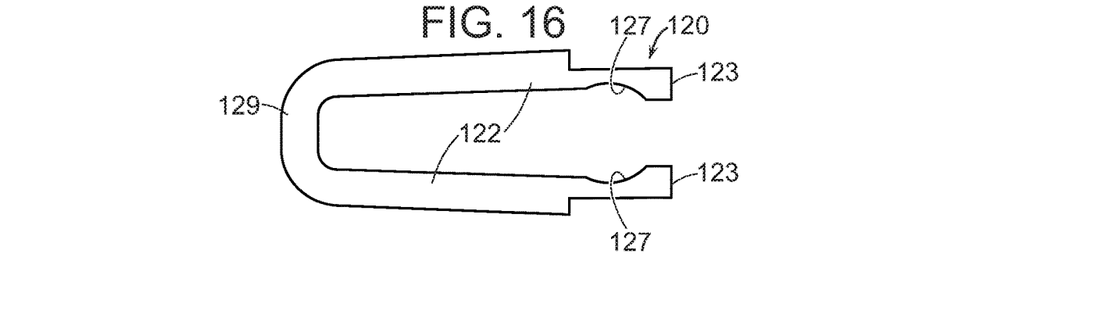
FIG. 16 is a plan view of an lower implant retainer that holds a lower implant in the cartridge.

The implants for each tissue clamp are held, releasably, in the cartridge 108 by U-shaped retainers, including an upper retainer 118 (FIG. 15) that holds the upper implant and a lower retainer 120 (FIG. 16) that holds the lower implant. Each retainer has a pair of legs 122 that are slidably mounted to and extend through apertures 121, 123 formed in a rear cartridge wall 124 so that the free ends 123 of the retainer legs 122 extend toward the front face 110 of the cartridge. A rear cover 125 may be attached to the rear wall 124 to define a chamber 127 that provides space that receives the bights 129 of the retainers (FIG. 12). The free ends of the legs 122 of the upper retainer 118 are spaced so that they will embrace and engage the tubular body 48 of the upper implant 44 to hold the upper implant, releasably, in the cartridge. The inwardly facing surfaces at the ends of the legs of the upper retainer 118 preferably are contoured at 125 to mate with the curved sides of the tubular body 48. Similarly, the free ends of the legs 122 of the lower retainer 120 are spaced and contoured, at 127, so that they will embrace and engage the waist 90 of the lower implant 46 to hold the lower implant, releasably, in the cartridge. The ends of the legs of the lower retainer 120 may be contoured to fit against the waist 90 of the protector 68. The legs of the upper and lower retainers are flexible to allow the free ends to separate and release their grip on the implants. The implants are transferred from the cartridge 108 to the deployment tool by inserting the forward ends 131 of the jaws 74, 82, 72 of the tool into the slots 112, 114, 116 of the cartridge. As the jaws are inserted, the fingers 126, 128 of the lower and intermediate jaws that define the slots 94, 84 engage the free ends of the legs 122 of the retainers to push the U-shaped retainers 118, 120 backward through the apertures 121. 123 toward the back of the cartridge as the slots 94, 84 advance to engage and grip the implants. The legs of the retainers 118, 120 flex to progressively release their grip on the implants as the jaws 74, 82 progressively establish their grip on the implants. Additionally, the rear cartridge wall 124 is formed to have front-extending stops 133, 135 placed to provide backup support for the implants to prevent them from moving rearwardly as the jaws are advanced forwardly into the cartridge slots. The uppermost cartridge slot 130 is adapted to receive the upper jaw 72 and may include a ramp 132 to guide the upper jaw so that it will not interfere with the engagement of the upper implant subassembly with the intermediate jaw. Once the upper and lower implants have been transferred to the deployment device, the handles can be operated to separate the jaws in readiness to receive tissue layers to be clamped.

With the deployment device loaded with the desired number of upper and lower implants, and with the deployment tool separated from the cartridge, the handles 78, 80 are operated to open the lower and intermediate jaws. The intermediate jaw moves together with the upper jaw because of its connection by the post 100. With the lower and intermediate jaws opened they can receive an atrial appendage 16 or other hollow anatomical structure or multi-layered tissue as suggested in FIG. 14. The handles 78, 80 then may be operated to close the jaws. The lower and intermediate jaws maintain the implants in alignment so that as the jaws are closed the upper jaw 72 will drive the locking pin 56 through the tissue layers and into the lower implant 46 until the locking elements 62, 64 lock the pin 56 and implants 42, 44 together.

FIGS. 17 and 18 illustrate tubular tissue T clamped between the interdigitated fingers 52, 54, illustrating the manner in which the interdigitated legs constrain clamped tissue in a serpentine configuration, interweaving in alternating directions over and about the legs. This configuration defines and results in a sealed zone that circumscribes the transfixing hole formed through the tissue T resulting from the deployment. The serpentine seal is effective to prevent blood from leaking through the hole. This is particularly important when occluding an atrial appendage, as one of the key problems with common suturing or stapling techniques, or the use of ligating clips is that they may cause or enable bleeding when the patient is taken off the heart-lung bypass machine. Uncontrolled bleeding requires the patient to be put back on the heart-lung machine while an effort is made to repair the leakage, increasing risk to the patient.

An additional feature of the interdigitated implants is that the serpentine configuration typically extends radially beyond the diameter of the implant such that sealed zone may extend to a diameter greater than that defined by the length of the legs 52, 54 of the implants. Consequently, when a plurality of implants are placed, for example, to create an elongated tissue seal as to seal an LAA, the implants can be spaced and do not have to overlap or be placed with extreme precision next to or in contact with each other.

Another complexity relating to occlusion of an atrial appendage is that the thickness of the walls of the appendage (and also, potentially, with other tissues) may vary from one location to another. The legs of the implants preferably are formed to have sufficient flexibility to allow them to flex to and self-adapt to variations in tissue thickness.

Importantly, because the tissue clamps, when placed individually, can each be placed at a location of the clinician's choosing, they do not have to conform to a linear path along the LAA or other structure to be closed off. The occluders can be used to create a non-linear line of occlusion. This is especially important for atrial appendage procedures because the ostium of the atrial appendage typically is non-linear. The occluders are thus more effective than linear hairpin-like clamps known in the prior art. Allowing the occluders to be placed non-linearly along the orifice of the LAA enhances the ability to avoid the creation of residual recesses where a clot can form. Linear clamps cannot follow the natural shape of the orifice and thus may leave recesses where blood can stagnate and result in later embolization.

From the foregoing, it should be appreciated that the invention provides new and improved tissue clamping devices and techniques adapted to transfix tissue layers and effect a seal between the clamped layers and about the points of transfixion. The invention is useful to secure tissue layers together and is particularly useful to occlude hollow anatomical structures, for example, as an atrial appendage. It should be understood, however, that the foregoing description of the invention is intended merely to be illustrative and that other embodiments, modifications and equivalents may be apparent to those skilled in the art without departing from its principles.

We claim:

1. A tissue clamp comprising:
an upper implant having a tubular body and a plurality of legs extending radially outward from the tubular body;
a lower implant having a tubular body and a plurality of legs extending radially outward from the tubular body, the upper and lower implants being operatively associated with each other and being adapted to clamp tissue layers disposed between the legs of the upper and legs of the lower implants, the lower tubular body having a first locking element;
a separate locking pin movable through the tubular bodies of the upper and lower implants and through tissue layers disposed between the implants, the locking pin having a second locking element formed thereon, the first and second locking elements being configured to lock together; the locking pin having an upper portion engageable with the upper implant to secure the position of the implants together when the locking elements are locked together.

2. A tissue clamp as defined in claim 1 wherein the upper portion of the locking pin engageable with the upper implant comprises: the upper portion of the locking pin having a head spanning a diameter greater than the inner diameter of the tubular body of the upper implant.

3. A tissue clamp as defined in claim 1 further comprising: the locking pin having a lower end that is sharp and adapted to pierce tissue.

4. A tissue clamp as defined in claim 3 further comprising a tissue protector attached to the lower end of the lower implant.

5. A tissue clamp as defined in claim 1 wherein, when the upper and lower implants are locked together in the absence of tissue, the legs of the upper implant are interdigitated with the legs of the lower implant between the legs.

6. A tissue clamp as defined in claim 5 wherein legs of the implants have sufficient stiffness so that tissue disposed between the upper and lower implants is constrained by interdigitated legs in a serpentine pattern that circumscribes the locking pin.

7. A tissue clamp as defined in claim 1 wherein the upper implant and locking pin comprise an upper implant subassembly, further in combination with a deployment tool, the combination comprising: the deployment tool comprising an intermediate jaw and a lower jaw, the jaws being movable toward and away from each other between an open position in which the jaws are receptive to tissue layers to be clamped to each other and a closed position in which the upper implant subassembly carried by the intermediate jaw and the lower implant carried by the lower jaw are brought together and connected to each other with the pin passing through and transfixing the tissue layers; the upper implant subassembly being releasably mounted to the intermediate jaw and the lower implant being releasably mounted to the lower jaw so that after the tissue clamp has been deployed in the tissue, the jaws can be separated from the upper implant subassembly and the lower implant.

8. The combination as defined in claim 7 further comprising: the deployment tool having an upper jaw above the intermediate jaw, the upper jaw having a pressure pad at its forward end, the upper jaw being movable toward the intermediate and lower jaws and being engageable with the upper portion of the locking pin, to drive the locking pin through the upper and lower implants and tissue layers clamped between the implants.

9. The combination as defined in claim 8 wherein the upper and lower jaws have a common pivot and where each of the upper and lower jaws have handles extending from the pivot.

10. The combination as defined in claim 9 further comprising a first spring operatively associated with the handles to bias the handles and upper and lower jaws apart.

11. The combination as defined in claim 10 further comprising a second spring biasing the upper and intermediate jaws apart and a limit stop operatively associated with the upper and intermediate jaws to limit the extent to which the upper and intermediate jaws can be separated.

12. The combination as defined in claim 8 wherein a plurality of tissue clamps are mounted to the intermediate and lower jaws.

13. The combination as defined in claim 12 wherein each of the tissue clamps is configured so that when the upper and lower implants are locked together, the legs of the upper implant are interdigitated with the legs of the lower implant to constrain the clamped tissue layers in a serpentine pattern that circumscribes the locking pin and extends radially beyond the extremities of the legs whereby a sealed zone may be effected that extends beyond the diameter defined by the implant legs.

14. The combination as defined in claim 13 wherein the deployment tool is configured to space adjacent tissue clamps in sufficient proximity so that, when deployed, their sealed zones will overlap.

15. The combination as defined in claim 7 further comprising a cartridge releasably holding an upper implant subassembly and a lower implant in readiness to be transferred in unison to the deployment tool, the cartridge having a front face with slots that are adapted to face and receive the jaws.

16. The combination as defined in claim 15 further comprising the intermediate and lower jaws having forwardly opening slots at their forward ends, the slots being configured to receive the upper implant subassembly and lower implant, respectively, the intermediate and lower jaws having retention members adapted to releasably retain the upper implant subassembly and lower implant within their respective slots after transfer from the cartridge to the deployment tool.

17. The combination as defined in claim 15 further comprising: the upper and lower implants being held in the cartridge in an unlocked configuration and with their legs interdigitated.

18. The combination as defined in claim 15 further comprising: the cartridge having a wall; an upper implant retainer and a lower implant retainer, both being movably mounted to the wall, the implant retainers being U-shaped having a pair of legs extending through and being slidable within apertures in the cartridge wall, the legs having free ends that extend toward the front face of the cartridge, each upper implant subassemblies and lower implants being held, releasably, between the free ends of the retainer legs.

19. The combination as defined in claim 18 further comprising; each of the implant retainers being mounted with its legs extending, slidably, through apertures in the wall.

20. The combination as defined in claim 19 further comprising: the forward ends of the intermediate and lower jaws being alignable with the free ends of the upper and lower retainer legs so that as the jaws are advanced into the cartridge, the jaws will engage the free ends of the retainer legs and will push the legs backward through the cartridge wall, thereby to cause the implant retainer legs to release the upper implant subassembly and lower implant as they are engaged by the slots of the jaws.

21. The combination as defined in claim 20 further comprising the cartridge wall having a front-extending stop associated with each of the upper implant subassembly and lower implant to maintain their respective positions as they are transferred from the cartridge to the deployment tool.

22. The combination as defined in claim 21 further comprising the cartridge and jaws of the deployment tool having cooperative guides to align the cartridge and jaws.

23. The combination as defined in claim 15 wherein the cartridge has an upper slot receptive to the upper jaw, the upper slot having a ramp to adjust the spacing of the upper jaw relative to the intermediate jaw.

24. A method for occluding a hollow anatomical structure in a human body comprising: providing a plurality of tissue clamps, each comprising an upper implant having a tubular body with a plurality of legs extending radially of the body and a lower implant having a tubular body and a plurality of legs extending radially of the body, the tubular body of the lower implant having a first locking element, and a separate locking pin movable through the implants and for piercing and transfixing opposing walls of the hollow structure and having a second locking element engageable with the first locking element for locking the implants together; the locking pin having an upper portion engageable with the upper implant to secure the position of the implants together when the locking elements are locked together; applying each of the tissue clamps to opposing walls of the hollow anatomical structure with the legs of the upper implants and lower implants in engagement with the external surfaces of the hollow anatomical structure;

advancing the locking pin through the implants and tissue to transfix the hollow anatomical structure and to lock the upper and lower implants together.

25. A method for occluding a hollow anatomical structure in a human body as defined in claim 24 wherein the plurality of tissue clamps are applied to define a line that seals and isolates the hollow anatomical structure.

26. A method for occluding a hollow anatomical structure in a human body as defined in claim 24 wherein the plurality of tissue clamps are applied simultaneously.

27. A method for occluding a hollow anatomical structure in a human body as defined in claim 24 wherein the tissue clamps are applied individually.

28. A method for occluding a hollow anatomical structure in a human body as defined in claim 24, wherein when the upper and lower implants are locked together, the legs of the upper implant are interdigitated with the legs of the lower implant.

29. A method for occluding a hollow anatomical structure in a human body as defined in claim 28 wherein interdigitated legs of the implants have sufficient stiffness to constrain the opposing walls of the hollow anatomical structure in a serpentine pattern.

30. A method for occluding a hollow anatomical structure in a human body as defined in claim 29 wherein each of the tissue clamps effects a seal that circumscribes the locking pin to define a sealing zone that is greater in diameter than that of the legs of the implants and wherein the tissue clamps are spaced so that the sealing zones of adjacent tissue clamps at least partly overlap.

31. A method for occluding a hollow anatomical structure in a human body as defined in claim 24 wherein the hollow anatomical structure comprises an atrial appendage.

* * * * *